US012678196B2

(12) United States Patent
Walker et al.

(10) Patent No.: US 12,678,196 B2
(45) Date of Patent: Jul. 14, 2026

(54) MULTIFUNCTION MICRODERMABRASION WAND

(71) Applicant: ALTAIR INSTRUMENTS, INC., Ventura, CA (US)

(72) Inventors: Douglas W. Walker, Ventura, CA (US); John Hubble, Chiang Mai (TH); Brendalie Acosta, Ventura, CA (US)

(73) Assignee: Altair Instruments, Inc., Ventura, CA (US)

( * ) Notice: Subject to any disclaimer, the term of this patent is extended or adjusted under 35 U.S.C. 154(b) by 660 days.

(21) Appl. No.: 17/506,110

(22) Filed: Oct. 20, 2021

(65) Prior Publication Data

US 2022/0117632 A1 Apr. 21, 2022

Related U.S. Application Data

(63) Continuation-in-part of application No. 29/811,934, filed on Oct. 18, 2021, now Pat. No. Des. 1,053,351.

(60) Provisional application No. 63/094,290, filed on Oct. 20, 2020.

(51) Int. Cl.
*A61B 17/54* (2006.01)
*A61B 17/00* (2006.01)

(52) U.S. Cl.
CPC .... *A61B 17/54* (2013.01); *A61B 2017/00402* (2013.01); *A61B 2017/00761* (2013.01); *A61B 2017/00765* (2013.01)

(58) Field of Classification Search
CPC .......... A61B 17/54; A61B 2017/00761; A61B 2017/00402; A61B 2017/00765; A61B 17/545; A61B 2017/00747; A61B 2017/320004; A61B 18/14; A61B 2018/00452; A61B 2018/0047; A61B 17/320068; A61B 2017/00473; A61B 2017/320008; A61B 2217/005; A61B 2217/007; A61B 2018/00458; A61B 2017/32007; A61B 2017/320069; A61M 35/003

See application file for complete search history.

(56) References Cited

U.S. PATENT DOCUMENTS

| | | | |
|---|---|---|---|
| 6,030,374 | A | 2/2000 | McDaniel |
| 6,241,739 | B1 | 6/2001 | Waldron |
| 6,500,138 | B1 | 12/2002 | Irby et al. |
| 8,221,437 | B2 | 7/2012 | Waldron et al. |
| 10,278,733 | B2 | 5/2019 | Walker et al. |

(Continued)

*Primary Examiner* — Martin T Ton
(74) *Attorney, Agent, or Firm* — Rutan & Tucker, LLP; Kyle M. St. James

(57) ABSTRACT

A multifunctional microdermabrasion wand provides to the wand operator the capability to perform microdermabrasion of a skin surface while simultaneously delivering one or more skin treatment serums. The operator can also simultaneously deliver ultrasonic energy through the wand to the skin surface. The operational controls for the multifunctional wand provide for operator control of the quantity delivered of one or more serums. The system also provides operator control of the ultrasonic energy delivered by the wand and a feed back control system to maintain a preset energy delivery level. The wand allows for conducting microdermabrasion, serum infusion and ultrasonic energy delivery to the skin surface in any combination simultaneously as well as serially.

19 Claims, 4 Drawing Sheets

(56) References Cited

U.S. PATENT DOCUMENTS

| 11,110,260 | B1 * | 9/2021 | Shadduck | A61N 5/062 |
|---|---|---|---|---|
| 2007/0232987 | A1 * | 10/2007 | Diaz | A61M 35/003 |
| | | | | 601/2 |
| 2008/0009802 | A1 * | 1/2008 | Lambino | A61M 37/0015 |
| | | | | 604/173 |
| 2009/0221955 | A1 * | 9/2009 | Babaev | A61B 17/320068 |
| | | | | 601/2 |
| 2010/0121197 | A1 * | 5/2010 | Ota | A61B 17/320068 |
| | | | | 600/462 |
| 2010/0305495 | A1 * | 12/2010 | Anderson | A61M 1/08 |
| | | | | 604/289 |
| 2014/0323993 | A1 * | 10/2014 | Wilcox | B65D 83/0011 |
| | | | | 604/311 |
| 2015/0313993 | A1 * | 11/2015 | Bock | A61H 7/005 |
| | | | | 604/22 |
| 2016/0038383 | A1 | 2/2016 | Matsushita et al. | |
| 2016/0106580 | A1 * | 4/2016 | Banko | A61F 9/00745 |
| | | | | 604/22 |
| 2016/0331308 | A1 * | 11/2016 | Zhou | A61M 35/003 |
| 2018/0056095 | A1 * | 3/2018 | Messerly | H10N 30/886 |
| 2018/0303515 | A1 * | 10/2018 | Shadduck | A61B 17/320068 |
| 2019/0133642 | A1 * | 5/2019 | Ignon | A61B 17/54 |
| 2019/0290893 | A1 * | 9/2019 | Levy | A61M 35/00 |
| 2020/0384253 | A1 * | 12/2020 | Fia | A61M 35/003 |

* cited by examiner

FIGURE 3        FIGURE 4

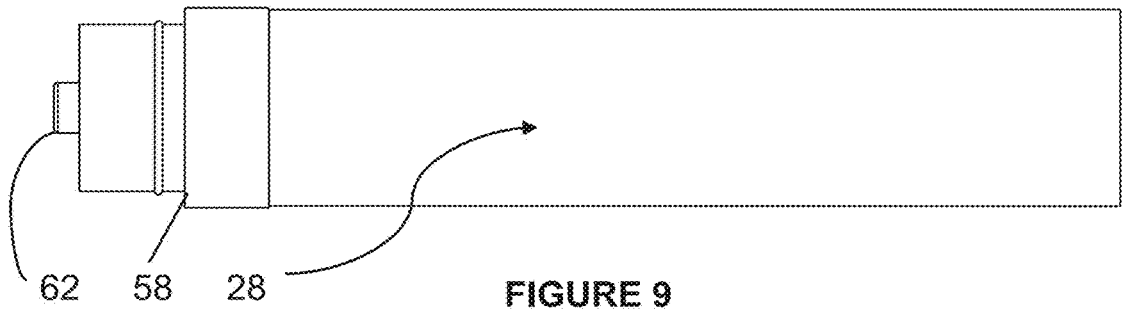
62    58    28                    FIGURE 9
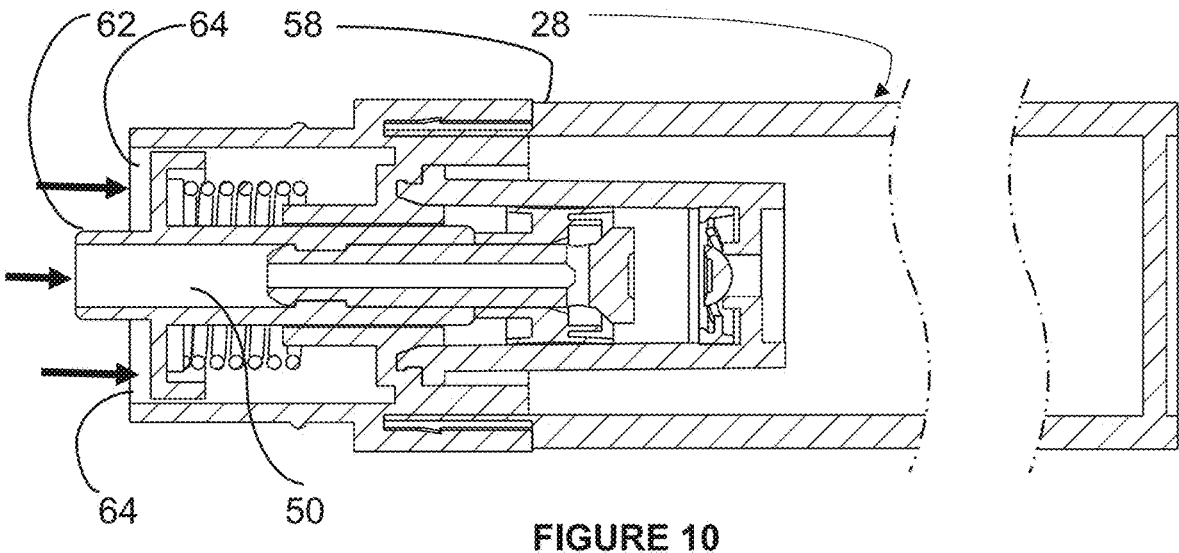
62    64    58              28
64         50              FIGURE 10

MULTIFUNCTION MICRODERMABRASION WAND

This application claims priority based on U.S. Ser. No. 63/094,290, filed Oct. 20, 2020, and is a Continuation-in-Part of U.S. Design application No. 29/811,934, file Oct. 18, 2021, which are incorporated herein in their entirety.

BRIEF DESCRIPTION

A multifunction microdermabrasion device to aid in the health, beauty and overall appearance of the skin provides a combination of microdermabrasion, serum infusion and phonophoresis. Microdermabrasion is a mechanical skin surface treatment or process for exfoliation or resurfacing the top skin layer, particularly the epidermis, and more specifically the Stratum Corneum. Serum application to the skin surface during or after microdermabrasion comprises coating of the skin surface or infusion through the skin surface of serums, lotions or nutritional products that are known to aid in or enhance the health and appearance of the skin (serums, lotions or nutritional products are all referred to herein by the term "serum"). The application of ultrasonic energy, also referred to as phonophoresis, when applied along with microdermabrasion and/or serums aids or enhance the efficacy of the microdermabrasion and/or serum application and/or processes. Described herein is a single device for delivering and/or applying these skin treatment techniques simultaneously, serially or as a combination of any two of these techniques.

BACKGROUND

Numerous devices have been described for providing microdermabrasion. In particular, reference is made to U.S. Pat. Nos. 6,241,739, 6,500,138, and 10,278,733. A device for vacuum enhanced skin treatment with a liquid is shown in U.S. Pat. No. 8,221,437.

U.S. Pat. No. 6,030,374 describes the use of ultrasound at low frequencies, from about 25 kHz and about 3 MHZ, in combination with other procedures to increase the permeability of the stratum corneum by various mechanical or abrasive methods. Examples of these could include microdermabrasion, for improving the transcutaneous or transdermal delivery of topical chemicals or drugs.

US Published Application 2016/0038383 discloses a combination of microdermabrasion, serum delivery and ultrasound.

BRIEF DESCRIPTION OF DRAWINGS

FIG. 3 is a front view of the multifunction microdermabrasion wand of FIG. 1 showing the abrasive tip and serum and vacuum ports.

FIG. 4 is a rear view of the multifunction microdermabrasion wand of FIG. 1.

FIG. 9 is a side view of the serum cartridge in its manually operable mode.

FIG. 10 is a longitudinal cutaway view of the cartridge as shown in FIG. 9.

DESCRIPTION

The use of therapeutic ultrasound to aid in the introduction of pharmalogical, healthcare and beauty serums, called phonophoresis, and has been medically documented. However, it's use has not been widely evaluated. The use of microdermabrasion of human skin with the concurrent delivery of ultrasonic energy is known. However, the multifunction microdermabrasion device described herein for performing microdermabrasion, serum delivery and providing ultrasonic energy incorporates several unique features not shown or contemplated in prior described devices. The delivery of serum and ultrasound in combination while performing microdermabrasion improves the skin surface treated by enabling greater transport of serum treatment molecules across cell membranes and through interstitial skin cells and layers.

Figure 1:
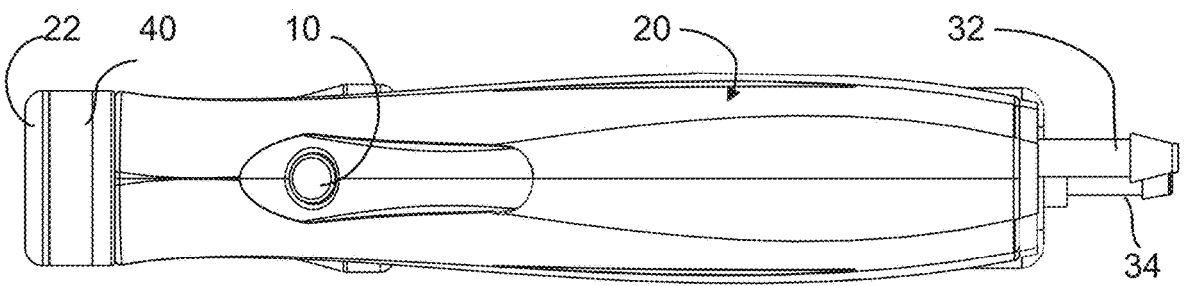
FIG. 1 is a top view of the multifunction microdermabrasion wand incorporating features of the invention.
Figure 2:
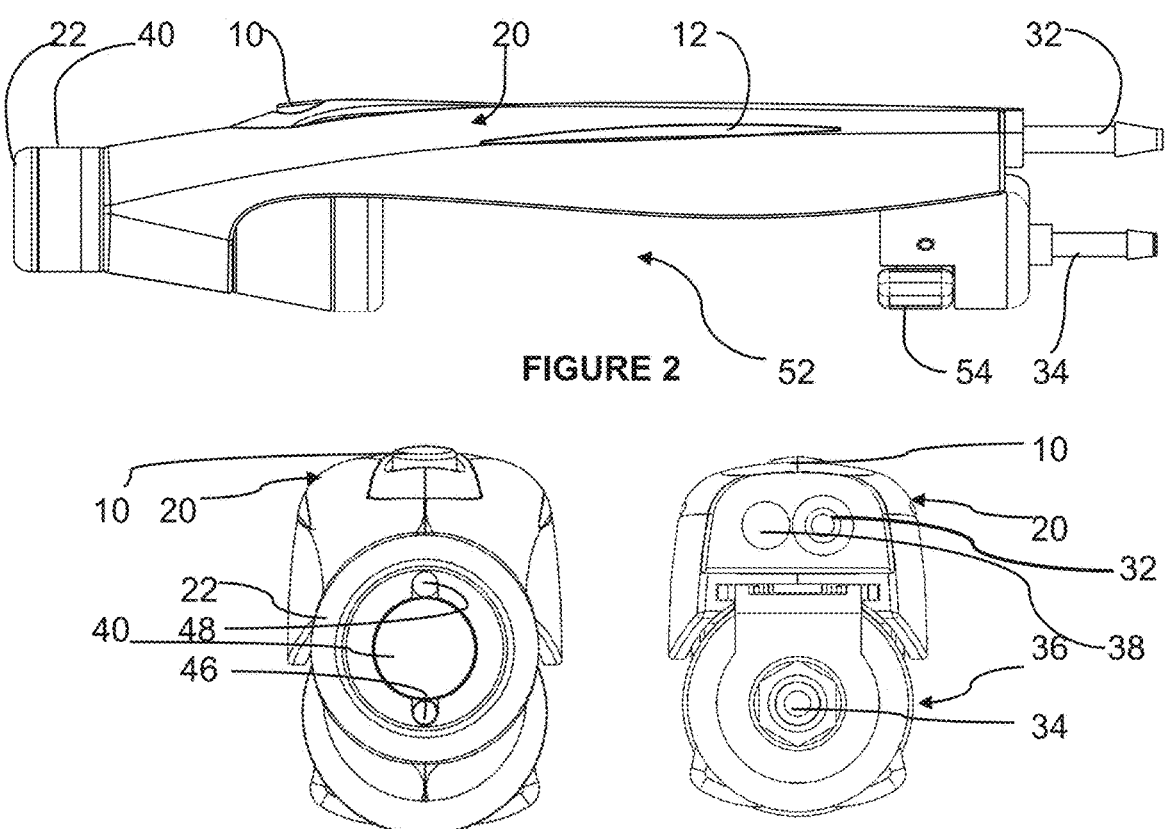
FIG. 2 is a side view of the multifunction microdermabrasion wand of FIG. 1.
Figures 5, 6:
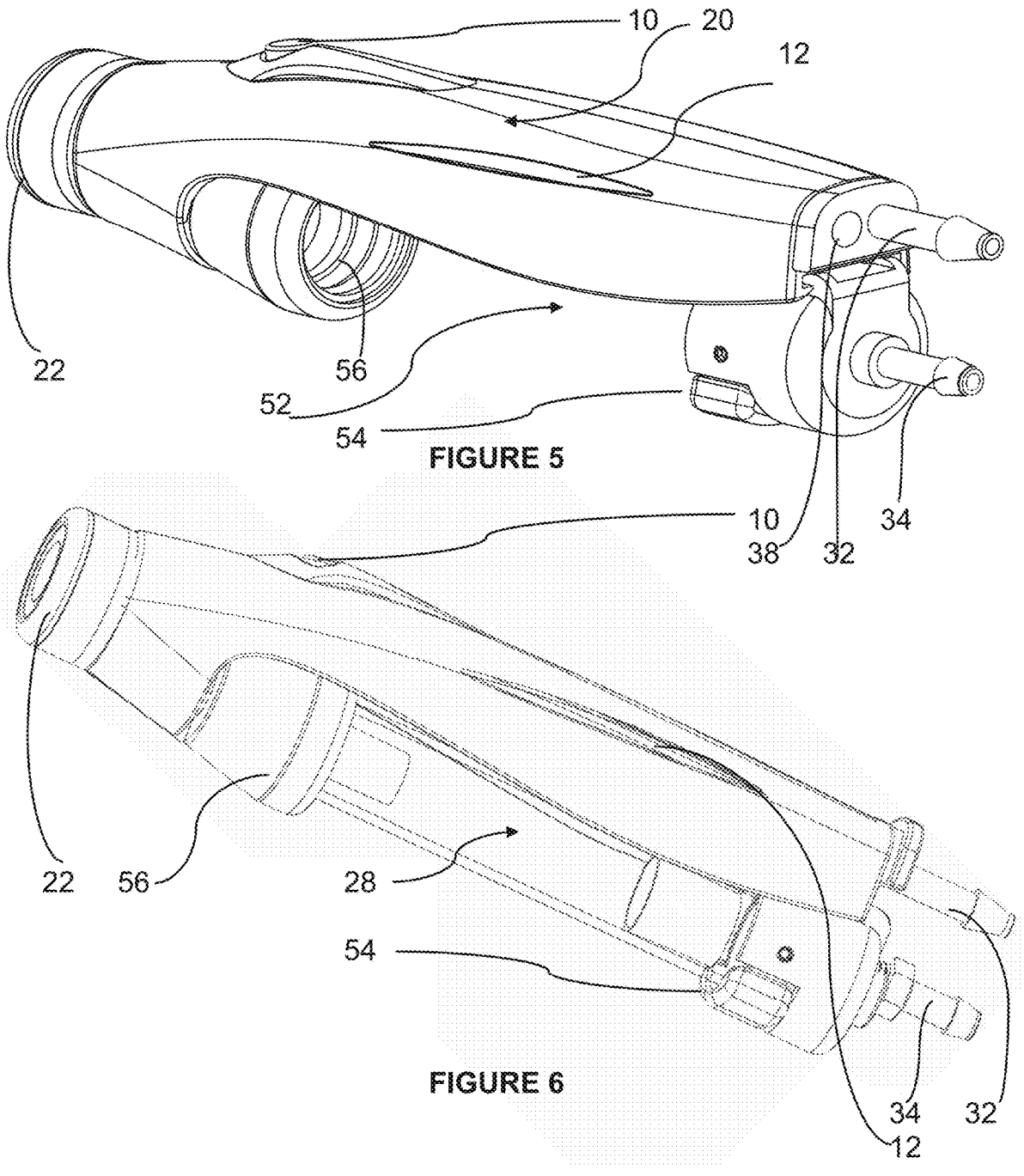
FIG. 5 is a side perspective view of the multifunction microdermabrasion wand of FIG. 1.
FIG. 6 is a side perspective view of the multifunction microdermabrasion wand of FIG. 1 with a transparent serum cartridge inserted therein.
Figure 7:
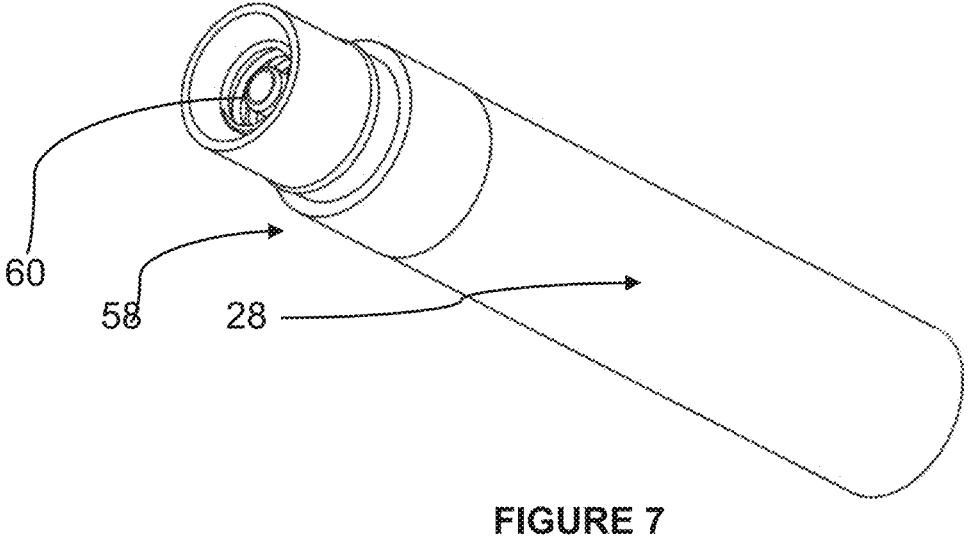
FIG. 7 is a side perspective view of a single serum cartridge for use in the multifunction microdermabrasion wand of FIG. 1 with the valve in the open position.
Figure 8:
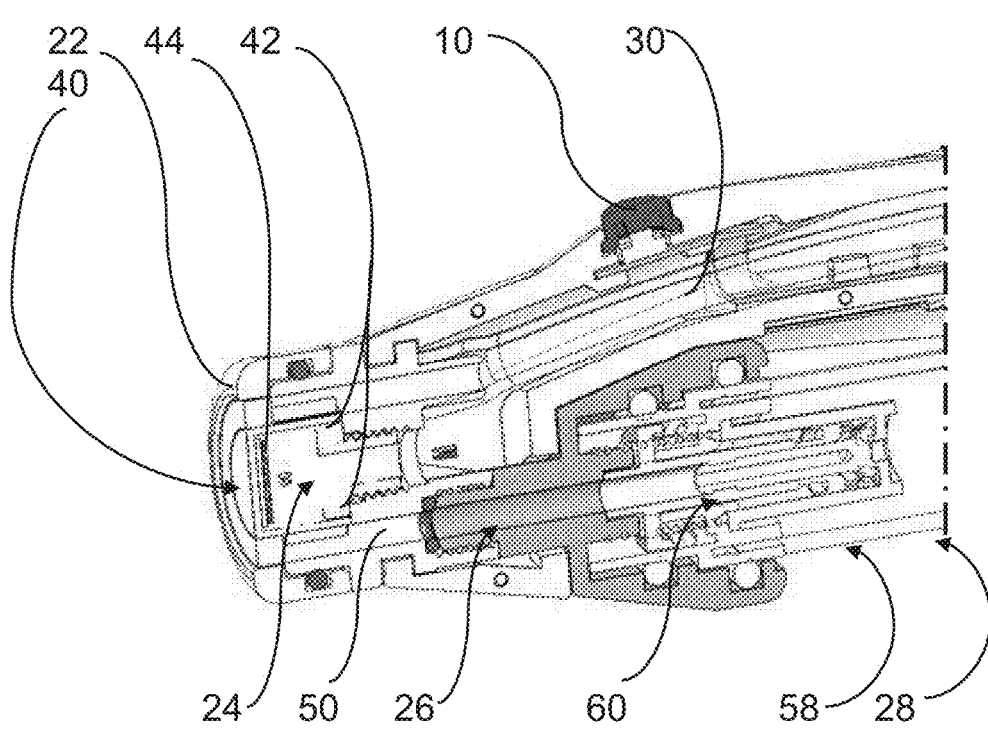
FIG. 8 is a cutaway view showing the internal forward portion of the multifunction microdermabrasion wand of FIG. 1.

FIGS. 1-4 show top, side, front and rear views, and FIG. 5 shows a perspective view of the multifunction microdermabrasion wand 20, all prior to insertion of a removeable serum cartridge in a lower portion thereof. FIG. 6 is a view of the wand with a transparent serum cartridge placed therein. An example of said cartridge with the valve in the forward end thereof in an open position is shown in FIG. 7. FIG. 8 shows a view of the forward portion of the wand, cut longitudinally along the length of the wand 20, with a side view of the abrasive microdermabrasion ring 22 on the tip (front) end 40, parts of the ultrasound assembly 24 and valve portion 8 within the top of the serum cartridge 28. A vacuum tube 30 is shown in the upper portion of the wand 20.

With reference to FIGS. 1-4 a user-operated on-off button 10 for activating and deactivating the wand functions is located on the top of the wand 20. Once the operation of the wand 20 is activated by the user pressing the on-off button 10, an LED light display in a light enclosure 12 is activated, different colors of the LEDs (such as red or blue) indicating the status of different functions of the wand 20.

As best illustrated in FIG. 4, the rear end 36 of the wand 20 includes a vacuum connector 32 for attachment of the vacuum tube 30 to an external vacuum pump, and input connector 34 for attachment of a pressure line to pressurize the serum (not shown) in the cartridge 28. Also located on the rear end 36 is an electrical port 38 for receiving an electrical conduit (not shown) for suppling power to the ultrasound assembly 24 located within the front end 40 of the wand 20 adjacent the abrasive microdermabrasion ring 22. The main components of the ultrasound assembly 24 are one or more piezoelectric elements (PZE) 42 and a piezo plate 44 which, in combination transmit ultrasonic energy through the tip (front) end 40 to the serum dispensed from the cartridge 28 and delivered to the skin surface being treated.

Not shown in the figures is an external control console including, but not limited to, a a) vacuum pump, and an external filter and fluid receptacle for extracting and capturing excess serum, debris, and skin from the treatment surface, b) an air pump, bottled gas source or similar source of pressurized gas to drive the serum from the cartridge located in the wand, and c) special software programs for controlling and varying the delivery of the ultrasonic energy and the delivery of the serum from the one or more serum cartridges.

Table 1 lists examples of the PZE operating parameters that are controlled in and on the control console by the software and operator adjustments. A standard PZE pulse width is about 12 msec.

TABLE 1

Examples of Piezo Operating Parameters

| Setting | Pulse amplitude-Enable | Period (msec.) | Frequency (Hz) | Duty Cycle (%) |
|---|---|---|---|---|
| Low | +5 | 600 | 1.667 | 2 |
| Medium | +5 | 240 | 4.167 | 5 |
| High | +5 | 120 | 8.333 | 10 |
| Demo* | +5 | na | na | na |

*In the Demo mode, a 2.0 second 100% burst, is provided for preoperational purposes.

Ultrasonic energy is usually provided by piezo-electric ceramic components operating at the 1-10 MHz range but, according to medical literature, may also be in the 10-100 kHz range. The piezo-electric (PZE) element is a thin disc or ring of various ceramic alloy composition that converts a high frequency electrical signal into a mechanical vibration. The thinness of the PZE determines its resonance frequency, while the voltage signal determines its amplitude. A piezo-electric element has only one resonant frequency with a range that can be quite small. The PZE is bonded onto or in contact with a tip or head 40 used to conduct (transmit) that vibration. The mass of the assembly can lower the resonant frequency slightly, with the thinness of the head determining how much mechanical vibration there is. At higher than >1 MHz frequency only the surface directly above the PZE vibrates.

In a preferred embodiment the piezo-ceramic element (PZE) is centrally located adjacent the tip of the wand. A circular ring or element 22 has an abrasive material, such as diamond crystals, attached to at least its forward skin-contacting surface for skin resurfacing/microdermabrasion, the circular ring 22 encircling the PZE. A flow channel 50 is located between the centrally located PZE within the tip 40 and abrasive surfaced ring 22 to provide both serum infusion (positive) flow and negative pressure (vacuum) for removal of excess serum and skin debris. One or more positive and negative flow ports 46, 48 in the tip 22 are connected to the flow channel 50 and the vacuum tube 30 within the wand 20 to provide distribution of the serum across the skin. Only one positive flow port 46 and one negative flow port 48 are shown in FIG. 3. However multiple positive ports 46 and negative ports 48 are distributed circumferential on the tip 40. In a preferred embodiment they are opposite each other or the input and output channels alternate in a circumferential portion of the tip 40 and are connected to the internal flow channel 50 and vacuum tube 30. The flow channel 50 may be filled with a porous or wicking material (not shown), such as an open cell foam, which also enhances serum infusion. The porous material or pad can also act as a filter for large debris.

Using the multifunction microdermabrasion wand 20 described herein ultrasonic energy applied to the skin is usually delivered in the 1-10 MHz range, preferably at a frequency of about 4 MHz frequency or more, to the top layer of skin. Some of the benefits of using ultrasonic energy is that it provides enhance absorption of analgesics, skin serum or other topically applied compositions through both the interstitial cell layers and the internal cell membrane, targeting both the surface area where the serum is delivered as well as deeper skin layers.

While some prior art documents suggest heating the skin surface may be beneficial for delivering topically applied compositions a possible negative effect of ultrasonic applications can be that the applicator tip may become heated and the frequency used for delivery of the ultrasonic energy thus needs to be controlled and optimized. Ultrasound delivery may require the use of different frequencies for the delivery of different serums or type or form of serum as well as the condition of the skin tissue layers.

In a preferred embodiment one or more piezo-ceramic elements (PZE) are bonded to the underneath surface of a very hard material (metal or ceramic) applicator tip and the structure is insulated from the outside environment to prevent electrical shorting. The tip can also function as a skin resurfacing or micro-dermabrasion wand tip which can have abrasive materials bonded thereto. Electrical current, via high frequency AC signals, is applied to the electrically insulated PZE. The microdermabrasion tip may or may not also be electrically grounded.

One or more centrally located vacuum channels (tubes) 30, which are connected to an external vacuum source, are located within the multifunction microdermabrasion wand 20 that includes the other functional components described herein. These channels are used to remove debris and excess fluids from the skin surface.

The serum or other treatment compositions are provided as a fluid from a container, preferably removable and replaceable, within the multifunction microdermabrasion device. One or more flow channels 50 connect the serum cartridge 28 to one or more ports 46 in or adjacent the applicator tip for delivery of the serum, etc. to the skin surface being treated. The fluid delivery, circulation and dispersion are provided by a variable controlled vacuum and air flow or, in the alternative, the delivery of the fluid is provided by applying a controlled positive pressure to a fluid container or the contents in the container.

The design of the multifunction wand 20 allows the rapid change and insertion of the front end 58 of a serum cartridge 28 into a cartridge mount adapter 56 in a front area of the cartridge receiver portion 52. The inserted cartridge 28 is easily removed by manually operating the cartridge release 54. This is of particular benefit to the user as it provides the ability to use different serums on different skin types or skin areas during the same treatment session. FIG. 7 shows a flow control valve 60 located within front end 58 of the cartridge 28. In an alternative embodiment (not shown) the wand is designed to receive two different serum dispensers side by side so the user can rapidly alternate between two different serums.

FIG. 9 is another image of the serum cartridge 28 before installation into the cartridge mount adapter 56 with the flow control valve 60 in the closed position as evidenced by the valve tip 62 in its extended orientation. In this configuration the serum can be manually released from the cartridge by pressing (see arrows in FIG. 10) on the valve tip 62 or the spring-loaded plate 64 adjacent thereto which allows the serum in the cartridge 28 to flow by gravity through the flow control valve 60, particularly if the if the interior of the cartridge is pressurized. Pressing on the valve tip 62 and/or the spring-loaded plate 64 also creates a pumping action by applying compression to the serum in the cartridge causing the serum to flow. The ability to manually express the serum from the cartridge is particularly advantageous at it allows the wand operator to sample the serum in the cartridge before use.

The cartridges 28 are designed so that the contents thereof can be dispensed by applying external gas pressure thereto. For example, the cartridge 28 can contain a plastic bag filled with serum, the bag being compressed by application of gas pressure to the bag walls. In another embodiment, the cartridge 28 has a double bottom with an inner bottom slidable in the cartridge 28 and moveable to expel the serum contained therein. The second (external) bottom, which provides a sealed bottom to the cartridge, has an air hole in its bottom for delivery of compressed gas to drive the slidable/movable inner bottom. The air hole allows for delivery of positive gas pressure that then exerts force on the inner bottom and the contained fluid for serum delivery to the skin surface. The use of positive pressure serum infusion (delivery) provides the optimum level of fluid coverage onto the ultrasonic tip. This enhances and improves the therapeutic effects of ultrasonic microdermabrasion.

Using regulated, monitored, positive infusion pressure allows greater control of the treatment process by the operator. This greater control is of benefit to the skilled operator as he or she can tailor the treatment to an individual's skin type, or throughout the treatment applied to various skin tissue types. Skin thickness, condition, moisture content and sensitivity can vary from person to person, and within each person. For example, the skin on an individual's face varies from a person's cheek to temple to chin; the controls for the wand features allows varying the treatment parameters guided by analysis set forth in published medical reports. Also, the use of regulated and monitored positive infusion pressure allows a greater variety of skin serums and lotions to be used. Various serums differ in consistency, particulate levels, and viscosities. Therefore, by varying the positive feed pressure a wide variety of different serums can be used.

Several features and benefits of the multifunction microdermabrasion device are the use of one or more ring shaped PZE which allows equilateral, simultaneous and uniform infusion of serums. The concentric ring shape of the PZE enhances and maximizes the delivery of the ultrasonic energy as the ring shape evenly applies the energy to the treatment area. The use of the ring shaped PZE also provides enhanced delivery of the ultrasonic energy for vacuum assisted, fluid free, crystal microdermabrasion by allowing application of the vacuum to be evenly applied across the abrasive surface being utilized. The design of the wand also allows the ultrasonic tip to be cooled and excess heat to be removed during the ultrasonic energy delivery. The applied serum also circulates during ultrasonic delivery removing heat from the tip, providing better comfort and safety to the end user and the individual being treated.

The use of two or more PZE 42 in the tip 40 provides the capability to deliver different ultrasonic frequencies without the need to change devices or handpiece tips. Different frequencies can have different benefits depending on the serum being applied, the skin condition or other variables. Different ultrasonic power levels can also be delivered based on changing duty cycles of the given or tuned ultrasonic piezo-ceramic tip.

Additionally, providing a small groove cut into the top of the infusion head (not shown) acts as a dispersion channel for the serum or lotion to flow through. This allows a more thorough and even distribution of fluid and allows better thermal properties, especially cooling properties of the head or tip.

Alternative embodiments can include interchangeable heads to allow the tips to be readily mounted, replaced or exchanged around a central ultrasonic unit. Dual or multiple serum inputs (infusion) and outputs (vacuum/suction) tubes can also be positioned around the center ultrasonic (PZE) head to facilitate flow over and around the ultrasonic head. A filter and/or wetting element can also be added to the tip, which is similar in purpose to the filter tip on the hydrowand disclosed in applicant's earlier U.S. Pat. No. 8,221, 437. The filter functions to provide a wetting element so that serum is constantly applied over the skin and in contact with both skin and the ultrasonic element at all times. The ultrasonic element also causes a misting evaporation and/or atomization to provide a constant presence of serum and improved infusion and penetration of serum into and through skin cells and tissue. The filter element in the wand 20 and the external control box also collects debris, dirt, impurities and other undesirable materials that can be generated from the skin surface by the tip due to the microdermabrasion procedures and from ultrasonic energy application to the skin surface.

The design of the wand tip allows uniform distribution of the ultrasonic energy to the skin surface as well as the application of multiple frequencies to the skin during treatment. This is beneficial as different frequencies have differing biological effects, and different serums can function differently with different levels of abrasion by the diamond coated tips. For example, ascorbic acid is shown in some studies to be more beneficial with 5 MHz energy while salicylic acid can work best at 1.0 MHz. Generally, the lower the frequency the deeper the depth of effective skin tissue treatment.

Because the cartridge 28 used to dispense the serum contained therein is readily interchangeable multitude different infusion serums can be applied simultaneously or serially depending on operator preference.

Additional technical functions and innovations include, but are not limited to, automatic tuning functions, automatic sensing and automatic tuning utilizing Phased Lock Loop (PLL) technology, and micro-processor controlled oscillating frequency generation and control.

Auto-tuning functions: When the ultrasonic head is brought into contact with substrate skin and/or serum the applied frequency can change, for example as a result of damping. This will result in a change in the overall frequency of the head and a shift away from the natural resonance frequency of the wand, thus lowering efficiency and output power of the transmitted ultrasonic energy. In the absence of the application of the intended level of energy the benefits intended for the ultrasonic wand such as a greater skin permeability by the applied serum and greater enhancement levels for serum infusion and microdermabrasion skin resurfacing are not obtained. The circuit design is programmed to sense the input frequency and compare it to what an efficient input resonant frequency should look like. By sensing the actual measured frequency and shifting the output frequency to a different resonant frequency closer to the intended operating parameters improved control of the procedure then results. This can be accomplished on a continuous real-time basis.

Automatic sensing and automatic tuning utilizing Phased Lock Loop (PLL) technology. The wand connected to the control box uses a feedback control system that generates an output signal related to an input signal and as a result detects, compares and adjusts the phase difference of the two signals. This provides both synchronization of the signals and tracking or recording of the differences between the two signals. These functions can then be used to deliver and optimized the resonant frequency of the ultrasonic head.

Micro-Processor Controlled Oscillating Frequency Generation and Control. The use of the signal data collection and storage allows one to optimize the resonant frequency of the ultrasonic head. This can then be used with other functions including:

a. The use of multiple oscillating modes and frequencies and/or the use of multiple ultrasonic or piezo-electric elements in an infusion or microdermabrasion head.
   b. The use of control circuitry to improve performance by relating the output signal to the different characteristics of different wand attachments. This can also be based on characteristics of the abrasive surface wand head attachment, infused serum or combination thereof. Also included are settings of designated levels of output voltage, power or signal based on data supplied. Also sensed (or manually entered into the control box are specific wand attachment identifications (makes and models) which allows the setting of corresponding technical functions based on that identification.
   c. The use of control circuitry allows improved overall performance and function of desired treatment. This includes safety functions such as over-voltage, over-current, or over-heating measurements, run time information and controls, either as a function of attachment performance or end user performance.
   d. The use of control circuitry also allows evaluation and tracking of ultrasonic and piezo-ceramic element performance, maintenance, and duration, including monitoring end life and replacement information. For example, the piezo-electric component material has a given life span which then can result in a significant degradation of performance thereafter. The system notifies the user of this condition, and a replacement or safety notice is provided.

The new multifunction microdermabrasion wand described herein combines the benefits of microdermabrasion using a tip with permanently bonded abrasive materials such as diamond crystals (disclosed in the Waldron '739 patent, incorporated herein by reference) attached to the tip surface, serum infusion (disclosed in Waldron '437 patent, incorporated herein by reference) and ultrasonic energy. The wand also provides enhanced skin treatment based on the synergist effect of the combination and the interactive electronically programed and independent operator designated operating functions.

We claim:

1. A multifunction microdermabrasion wand for treating a skin surface comprising:

a front end including an abrasive tip, one or more piezo-electric elements, a piezo plate, and a cartridge mount adapter,
      wherein the abrasive tip is configured for removing an outer portion of the skin surface, the abrasive tip comprising a crystalline material bound to a surface of the abrasive tip,
      wherein the one or more piezoelectric elements and the piezo plate are configured to combine to transmit ultrasonic energy to the skin surface, and wherein the cartridge mount adapter is configured to receive a front end of a first removable cartridge of one or more removeable cartridges, wherein the first removable cartridge contains a skin treatment serum;
   a back end including a rear housing configured to receive a rear end of the first removable cartridge, wherein an input connector extends outwardly from the rear housing and is configured to receive pressurized gas and provide the pressurized gas to the rear end of the first removable cartridge thereby driving a skin treatment serum from the first removable cartridge; and
   a cartridge covering component that extends from the front end to the back end and encompasses at least a portion of the first removable cartridge,
   wherein the multifunction microdermabrasion wand and the one or more removeable cartridges in combination are configured for controlled delivery of the skin treatment serum to the skin surface being treated.

2. The multifunction microdermabrasion wand of claim 1, wherein the back end includes a vacuum connector configured to attach to a vacuum pump, wherein the vacuum connector is configured to pass at least one of excess serum, debris, or skin cells toward the vacuum pump.

3. The multifunction microdermabrasion wand of claim 1, wherein the one or more piezoelectric elements is a disc or ring comprised of a ceramic alloy composition that is configured to convert a high frequency electrical signal into a mechanical vibration.

4. The multifunction microdermabrasion wand of claim 1, wherein the piezo plate is bonded onto or in contact with the abrasive tip.

5. The multifunction microdermabrasion wand of claim 1, wherein the piezo plate is located adjacent the abrasive tip.

6. The multifunction microdermabrasion wand of claim 1, further comprising:

a flow channel located between the piezo plate and the abrasive tip, wherein the flow channel is configured to provide at least one of serum infusion via a positive flow or suction via a negative pressure for removal of excess serum and skin debris.

7. The multifunction microdermabrasion wand of claim 6, further comprising:

a positive flow port having a distal point at the front end adjacent the abrasive tip and connected to the flow channel, wherein the positive flow port is configured to provide the serum infusion; and
   a negative flow port having a distal point at the front end adjacent the abrasive tip and connected to the flow channel, wherein the negative flow port is configured to provide the suction.

8. The multifunction microdermabrasion wand of claim 1, wherein the one or more piezoelectric elements are piezo-ceramic elements.

9. The multifunction microdermabrasion wand of claim 1, wherein the one or more piezoelectric elements are bonded to an underneath surface of an applicator tip thereby insulating the one or more piezoelectric elements from an outside environment.

10. The multifunction microdermabrasion wand of claim 1, wherein the first removable cartridge of the one or more removeable cartridges is configured to receive pressurized gas through a hole located on a side of the first removable cartridge.

11. The multifunction microdermabrasion wand of claim 10, wherein the first removeable cartridge includes a moveable inner bottom that is configured to move in response to receipt of the pressurized gas thereby causing delivery of the skin treatment serum to the skin surface.

12. The multifunction microdermabrasion wand of claim 1, wherein at least one of fluid delivery, circulation and dispersion are provided by a variable controlled vacuum or other air flow.

13. The multifunction microdermabrasion wand of claim 1, further comprising:

a cartridge receiver portion formed between the front end and the back end, wherein the cartridge receiver portion includes the cartridge mount adapter in a front area of the cartridge receiver portion.

14. The multifunction microdermabrasion wand of claim 13, wherein the cartridge mount adapter includes a cartridge release that is configured for manual operation.

15. The multifunction microdermabrasion wand of claim 13, wherein the cartridge mount adapter is configured to receive two serum cartridges in a side-by-side configuration.

16. The multifunction microdermabrasion wand of claim 1, wherein the one or more piezoelectric elements include two piezoelectric elements, wherein a first piezoelectric element is configured to provide a first ultrasonic frequency and a second piezoelectric element is configured to provide a second ultrasonic frequency different from the first ultrasonic frequency.

17. The multifunction microdermabrasion wand of claim 1, wherein a first removeable cartridge of the one or more removeable cartridges includes a valve tip configured to control flow of the skin treatment serum.

18. The multifunction microdermabrasion wand of claim 17, wherein the valve tip is configured to receive external pressure resulting in a manual express of the skin treatment serum.

19. A multifunction microdermabrasion wand for treating a skin surface comprising:

a front end including an abrasive tip, one or more piezoelectric elements, a piezo plate, and a cartridge mount adapter, wherein the abrasive tip is configured for removing an outer portion of the skin surface, the abrasive tip comprising a crystalline material bound to a surface of the abrasive tip, wherein the one or more piezoelectric elements and the piezo plate are configured to combine to transmit ultrasonic energy to the skin surface, and wherein the cartridge mount adapter is configured to receive a front end of a first removable cartridge of one or more removeable cartridges, wherein the first removable cartridge contains a skin treatment serum;

a back end including:

a rear housing configured to receive a rear end of the first removable cartridge, wherein an input connector extends outwardly from the rear housing and is configured to receive pressurized gas and provide the pressurized gas to the rear end of the first removable cartridge thereby driving a skin treatment serum from the first removable cartridge, and a vacuum connector configured to attach to a vacuum pump, wherein the vacuum connector is configured to pass at least one of excess serum, debris, or skin cells toward the vacuum pump;

a cartridge receiver portion adjacent the front end, wherein the cartridge receiver portion includes a cartridge mount adapter in a front area of the cartridge receiver portion and is configured to receive the one or more removable cartridges; and a cartridge covering component that extends from the front end to the back end and encompasses at least a portion of the first removable cartridge.

* * * * *